(12) United States Patent
Ruiz et al.

(10) Patent No.: US 7,872,169 B2
(45) Date of Patent: Jan. 18, 2011

(54) REDUCED NOISE LEVEL FASTENING SYSTEM

(75) Inventors: Oscar Antonio Ruiz, Mason, OH (US); John Carroll Molander, Montgomery, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 548 days.

(21) Appl. No.: 11/638,799

(22) Filed: Dec. 14, 2006

(65) Prior Publication Data

US 2007/0149938 A1    Jun. 28, 2007

Related U.S. Application Data

(60) Provisional application No. 60/753,101, filed on Dec. 22, 2005.

(51) Int. Cl.
*A61F 13/20* (2006.01)
(52) U.S. Cl. ............. 604/383; 604/385.29; 604/385.3; 604/389; 604/391
(58) Field of Classification Search ............. 604/383, 604/385.29, 385.3, 389, 391
See application file for complete search history.

(56) References Cited

U.S. PATENT DOCUMENTS

| | | | |
|---|---|---|---|
| 3,860,003 A | 1/1975 | Buell | |
| 3,911,173 A | 10/1975 | Sprague, Jr. | |
| 3,929,135 A | 12/1975 | Thompson | |
| 4,324,246 A | 4/1982 | Mullane et al. | |
| 4,342,314 A | 8/1982 | Radel et al. | |
| 4,463,045 A * | 7/1984 | Ahr et al. | 428/131 |
| 4,515,595 A | 5/1985 | Kievit et al. | |
| 4,568,344 A * | 2/1986 | Suzuki et al. | 604/389 |
| 4,573,986 A | 3/1986 | Minetola et al. | |
| 4,609,518 A * | 9/1986 | Curro et al. | 264/504 |
| 4,610,678 A | 9/1986 | Weisman et al. | |
| 4,629,643 A | 12/1986 | Curro et al. | |
| 4,673,402 A | 6/1987 | Weisman et al. | |
| 4,695,278 A | 9/1987 | Lawson | |
| 4,772,444 A * | 9/1988 | Curro et al. | 264/557 |
| 4,785,996 A | 11/1988 | Ziecker et al. | |
| 4,798,603 A * | 1/1989 | Meyer et al. | 604/378 |
| 4,834,735 A | 5/1989 | Alemany et al. | |
| 4,842,666 A | 6/1989 | Werenicz | |
| 4,846,821 A * | 7/1989 | Lyons et al. | 604/369 |

(Continued)

FOREIGN PATENT DOCUMENTS

CN    2291911 Y    9/1998

(Continued)

OTHER PUBLICATIONS pdf of patent family list of CN 2291911 Y; espacenet website / EPO (one page total).*

*Primary Examiner*—Tatyana Zalukaeva
*Assistant Examiner*—Ginger T Chapman
(74) *Attorney, Agent, or Firm*—Laura L. Whitmer

(57) ABSTRACT

A non-elastic thermoplastic film having a noise abatement region and a fastening component. The noise abatement region has a plurality of apertures, wherein each of the plurality of apertures has an area of between about 4 mm$^2$ to about 75 mm$^2$. The fastening component is disposed within the noise abatement region such that the fastening component is surrounded by the noise abatement elements.

11 Claims, 9 Drawing Sheets

U.S. PATENT DOCUMENTS

| | | | |
|---|---|---|---|
| 4,888,231 A | 12/1989 | Angstadt | |
| 4,892,536 A | 1/1990 | DesMarais et al. | |
| 4,909,803 A | 3/1990 | Aziz et al. | |
| 4,940,464 A | 7/1990 | Van Gompel et al. | |
| 4,946,527 A * | 8/1990 | Battrell | 156/60 |
| 4,968,312 A | 11/1990 | Khan | |
| 4,990,147 A | 2/1991 | Freeland | |
| 5,006,394 A | 4/1991 | Baird | |
| 5,037,416 A | 8/1991 | Allen et al. | |
| 5,062,840 A | 11/1991 | Holt et al. | |
| 5,092,861 A | 3/1992 | Nomura et al. | |
| 5,137,537 A | 8/1992 | Herron et al. | |
| 5,147,345 A | 9/1992 | Young et al. | |
| 5,151,092 A | 9/1992 | Buell et al. | |
| 5,171,236 A | 12/1992 | Dreier et al. | |
| 5,221,274 A | 6/1993 | Buell et al. | |
| 5,246,433 A | 9/1993 | Hasse et al. | |
| 5,260,345 A | 11/1993 | DesMarais et al. | |
| 5,269,775 A | 12/1993 | Freeland et al. | |
| 5,306,266 A | 4/1994 | Freeland | |
| 5,342,338 A | 8/1994 | Roe | |
| 5,387,207 A | 2/1995 | Dyer et al. | |
| 5,397,318 A | 3/1995 | Dreier | |
| 5,460,622 A | 10/1995 | Dragoo et al. | |
| 5,462,166 A * | 10/1995 | Minton et al. | 206/440 |
| 5,514,121 A | 5/1996 | Roe et al. | |
| 5,518,801 A | 5/1996 | Chappell et al. | |
| 5,540,671 A | 7/1996 | Dreier | |
| 5,554,142 A | 9/1996 | Dreier et al. | |
| 5,569,234 A | 10/1996 | Buell et al. | |
| 5,571,096 A | 11/1996 | Dobrin et al. | |
| 5,607,760 A | 3/1997 | Roe | |
| 5,609,587 A | 3/1997 | Roe | |
| 5,625,222 A | 4/1997 | Yoneda et al. | |
| 5,635,191 A | 6/1997 | Roe et al. | |
| 5,643,588 A | 7/1997 | Roe et al. | |
| 5,653,703 A | 8/1997 | Roe et al. | |
| 5,865,823 A | 2/1999 | Curro | |
| 5,897,545 A | 4/1999 | Kline et al. | |
| 5,938,648 A | 8/1999 | LaVon et al. | |
| 5,941,864 A | 8/1999 | Roe | |
| 5,957,908 A | 9/1999 | Kline et al. | |
| 5,968,025 A | 10/1999 | Roe et al. | |
| 5,977,430 A | 11/1999 | Roe et al. | |
| 5,997,520 A | 12/1999 | Ahr et al. | |
| 5,998,696 A * | 12/1999 | Schone | 604/378 |
| 6,013,063 A | 1/2000 | Roe et al. | |
| 6,120,487 A | 9/2000 | Ashton | |
| 6,120,489 A | 9/2000 | Johnson et al. | |
| 6,168,584 B1 | 1/2001 | Allen et al. | |
| 6,307,120 B1 * | 10/2001 | Glaug | 604/383 |
| 6,432,098 B1 | 8/2002 | Kline et al. | |
| 6,511,466 B1 * | 1/2003 | Nagami et al. | 604/389 |
| 6,680,422 B2 | 1/2004 | Roe | |
| 6,716,441 B1 | 4/2004 | Osborne et al. | |
| 2002/0103470 A1 | 8/2002 | Molander et al. | |
| 2003/0084996 A1 | 5/2003 | Alberg et al. | |
| 2003/0088220 A1 | 5/2003 | Molander et al. | |
| 2003/0233082 A1 | 12/2003 | Kline et al. | |
| 2004/0178544 A1 | 9/2004 | Jackson et al. | |
| 2004/0225273 A1 | 11/2004 | Ashton et al. | |

FOREIGN PATENT DOCUMENTS

| | | |
|---|---|---|
| WO | WO 94/14395 A1 | 7/1994 |
| WO | WO 95/16746 A1 | 6/1995 |
| WO | WO 95/24173 A2 | 9/1995 |

* cited by examiner

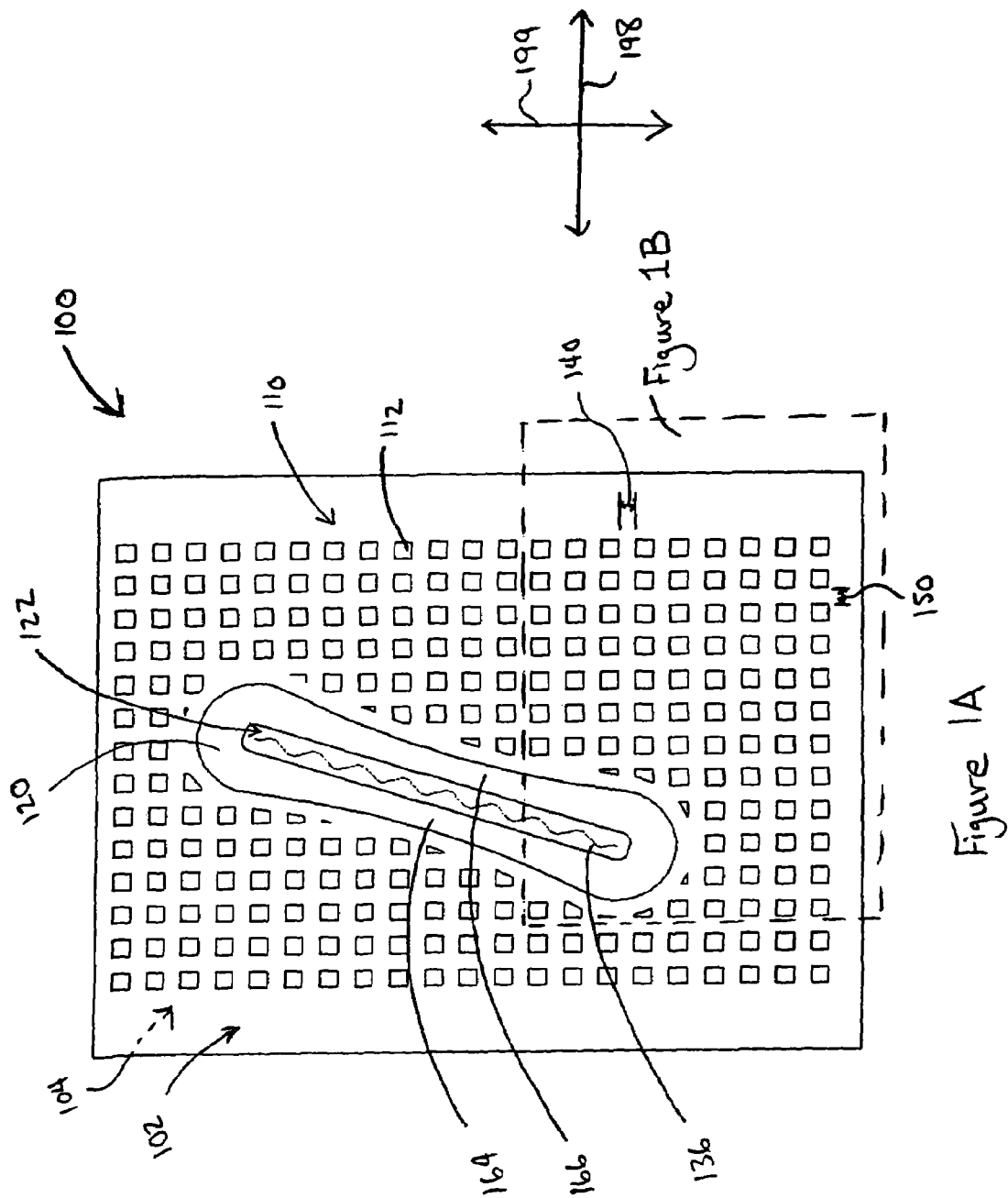

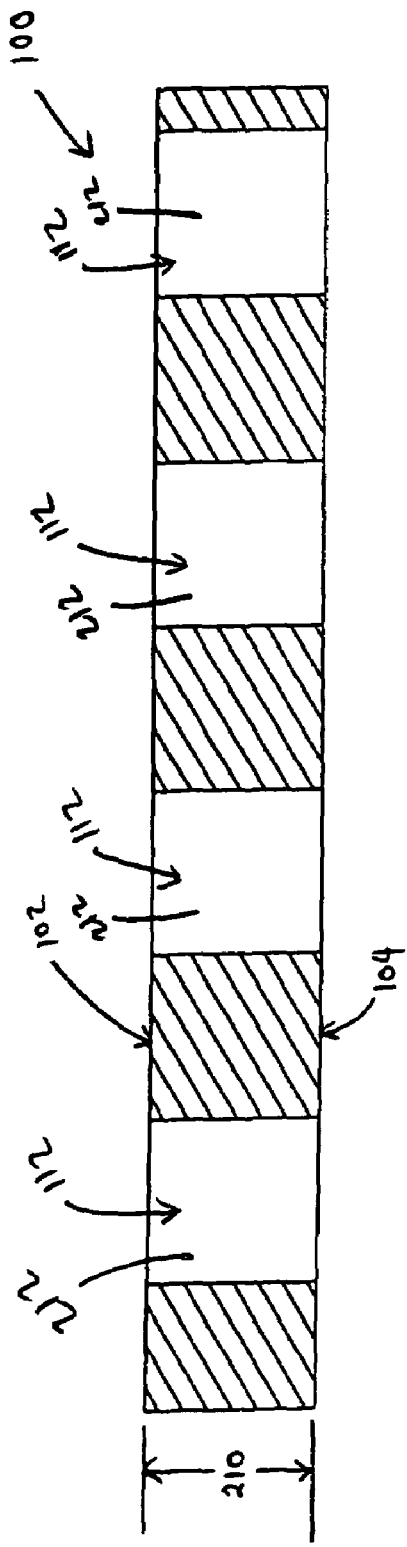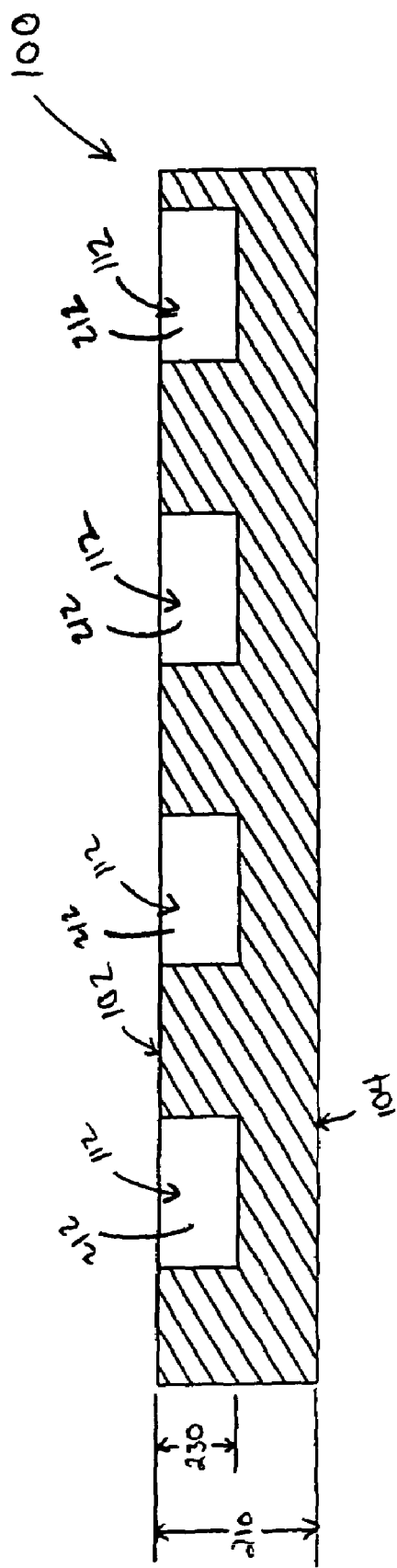
Figure 2A
Figure 2B

REDUCED NOISE LEVEL FASTENING SYSTEM

CROSS REFERENCE TO RELATED APPLICATIONS

This application claims the benefit of U.S. Provisional Application No. 60/753,101, filed Dec. 22, 2005.

FIELD OF THE INVENTION

The present invention pertains to thermoplastic films. Particularly, the present invention pertains to thermoplastic films exhibiting reduced sound intensities.

BACKGROUND OF THE INVENTION

Films are used in a number of consumer products. For example, disposable diapers can utilize films in a backsheet to prevent exudates from leaking out of the disposable diaper. Some disposable diapers can utilize films in their fastening systems.

Some films, particularly those used in a fastening system, can exhibit a crackling sound when exposed to expected fastening forces. Unfortunately, a consumer often associates this crackling sound with a lower quality product, thereby adversely affecting the consumer's perception of the product utilizing the film.

Consequently, a need exists for a film which exhibits reduced crackling sound intensities when subjected to expected forces. Additionally, a need exists for a disposable absorbent article utilizing a film which exhibits reduced the crackling sound intensities.

SUMMARY OF THE INVENTION

A film constructed in accordance with the present invention may exhibit reduced crackling sound intensities when subjected to expected forces. In one embodiment, the non-elastic thermoplastic film has a noise abatement region and a fastening component. The noise abatement region has a plurality of apertures, wherein each of the plurality of apertures has an area of between about 4 $mm^2$ to about 75 $mm^2$. The fastening component is disposed within the noise abatement region such that the fastening component is surrounded by the noise abatement elements.

In another embodiment, a disposable absorbent article may comprise a first waist region, a second waist region, a crotch region disposed between the first and second waist regions; a first waist edge and a second waist edge; and a first longitudinal edge and a second longitudinal edge. The disposable absorbent article may further comprise a topsheet a backsheet joined to at least a portion of the topsheet, and an absorbent core disposed between the topsheet and the backsheet.

The disposable absorbent article may further comprise a first pair of side panels and a second pair of side panels. The first par of side panels can extend outward from the first and second longitudinal edges in the first waist region, wherein each of the first pair of side panels comprises a first fastening component. The second pair of side panels can extend outward from the first and second longitudinal edges in the second waist region.

Each of the second pair of side panels may comprise a non-elastic thermoplastic film having a noise abatement region and a second fastening component. The noise abatement region may comprise a plurality of apertures, wherein each of the plurality of apertures has an area of between about 4 $mm^2$ to about 75 $mm^2$. The second fastening component disposed within the noise abatement region such that the fastening component is surrounded by noise abatement elements. The first fastening components are capable of engaging the second fastening components thereby fastening the disposable absorbent article.

BRIEF DESCRIPTION OF THE DRAWINGS

FIG. 1A is a plan view showing a non-elastic thermoplastic film constructed in accordance with the present invention.

FIG. 2A is a cross sectional view showing the non-elastic thermoplastic film of FIG. 1A along line 2A-2A.

FIG. 2B is a cross sectional view showing another embodiment of a non-elastic thermoplastic film constructed in accordance with the present invention.

DETAILED DESCRIPTION OF THE INVENTION

Figure 1B:
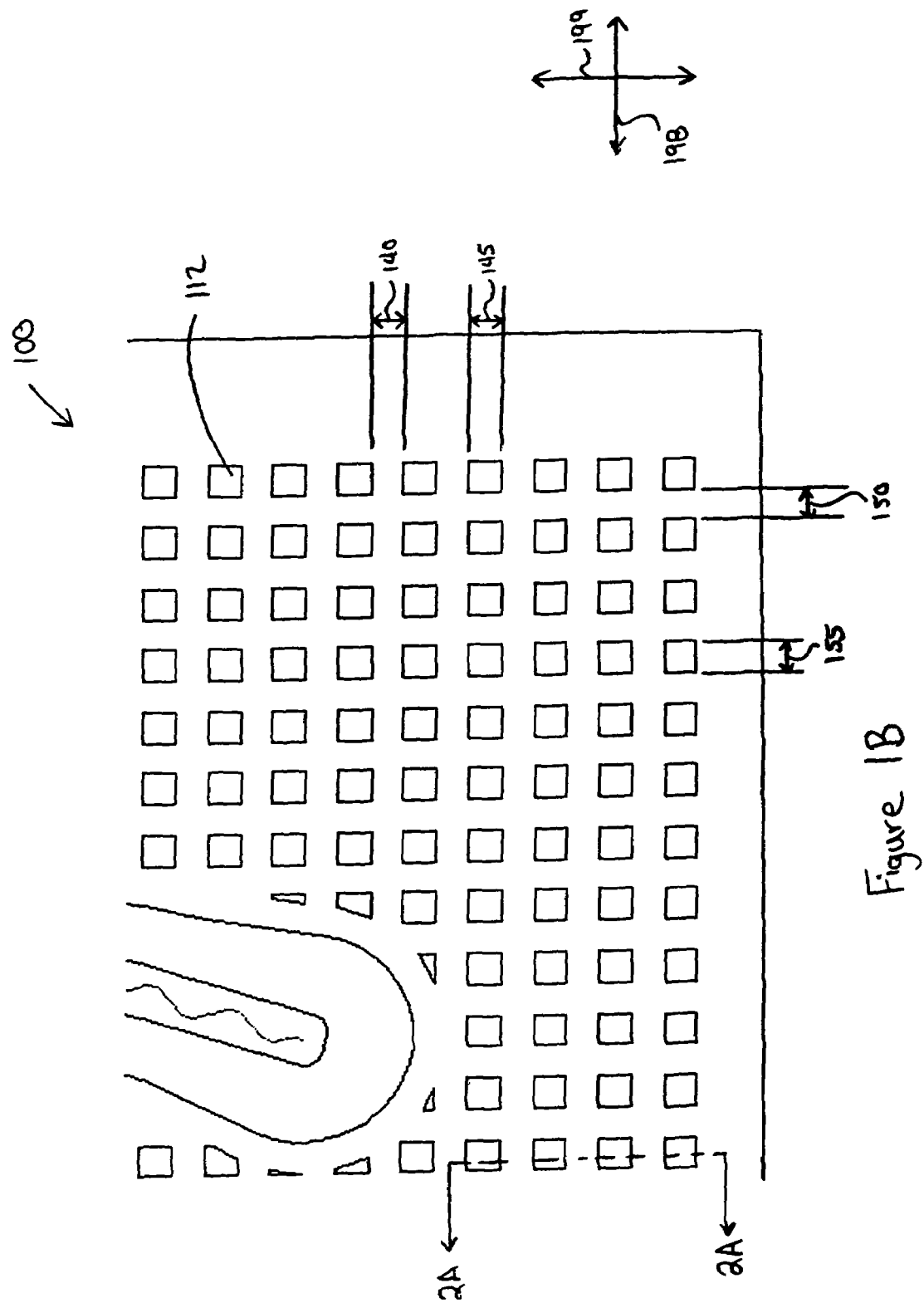
FIG. 1B is a close up view showing a portion of the non-elastic thermoplastic film of FIG. 1A.

Definitions:

As used herein, the terms "absorbent article" and "article" refer to a wearable device that absorbs and/or contains liquid and, more specifically, refers to a device that is placed against or in proximity to the body of the wearer to absorb and contain the various exudates discharged from the body. Suitable examples include diapers, training pants, refastenable pants, pull-on garments, adult incontinence products and feminine care products such as sanitary napkins. Furthermore, the terms "absorbent article" and "article" include a "disposable absorbent article" which is intended to be discarded and not laundered or otherwise restored after no more than ten uses, preferably after no more than five uses, and most preferably after a single use (although certain components may be recycled, reused, or composted).

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

As used herein "elastically extensible" refers to characteristics of extensible materials that have the ability to return to approximately their original dimensions after a force that extended the extensible material is removed. Herein, any material or element described as "extensible" may also be "elastically extensible" unless otherwise provided.

As used herein the term "joined" encompasses configurations whereby an element is directly secured to another element by affixing the element directly to the other element, and configurations whereby an element is indirectly secured to another element by affixing the element to an intermediate member(s) which in turn are affixed to the other element.

The term "longitudinal" is used herein to refer to a direction which is generally parallel to the longest edge of an element except where otherwise noted. In the context of disposable diapers, a "longitudinal" direction "runs substantially perpendicular from a waist edge to an opposing waist edge of the article and generally parallel to the maximum linear dimension of the article. Directions within ±45 degrees of the longitudinal direction are considered to be "longitudinal"

The term "lateral" refers to a direction running generally perpendicular to and in the same plane as the "longitudinal" direction. In the context of disposable absorbent articles, a "lateral" direction runs from one longitudinal edge of the article to an opposing longitudinal edge of the article. Directions within ±45 degrees of the lateral direction are considered to be "lateral".

The term "transverse" refers to a direction which is generally perpendicular to the plane of the longitudinal and lateral directions. Directions within ±45 degrees of the transverse direction are considered to be "transverse".

The terms "machine direction" or "MD" refer to a direction which is generally parallel to the forward direction of a material, member, element, item, etc. through a process. For example, nonwovens can be formed in a machine direction that corresponds to the long or rolled direction of fabrication. The machine direction can also be the primary direction of fiber orientation in the nonwoven.

The terms "cross direction" or "CD" refer to a direction which is generally perpendicular to and in the same plane as the machine direction.

The term "non-elastic thermoplastic" refers to a thermoplastic that can be melt processable and that returns to its original condition or near its original condition upon cooling and which does not exhibit elastomeric properties at ambient conditions (e.g., room temperature and atmospheric pressure). Additionally, the thermoplastic material will not substantially resume its original shape after being stretched by more than 20%.

The term "fibrous substrate" refers to a material comprised of a multiplicity of fibers that could be either a natural or synthetic material or any combination thereof. For example, nonwoven materials, woven materials, knitted materials, celluloid materials, and any combinations thereof are considered to be "fibrous substrates".

The term "non-fibrous substrate" refers to materials which do not comprise a multiplicity of fibers. For example, films, foils, foams, and the like are considered to be "non-fibrous substrates".

The terms "pant", "training pant", "closed diaper", "pre-fastened diaper", and "pull-on diaper", as used herein, refer to disposable garments designed for infant or adult wearers, wherein the disposable garments can have a waist opening and a pair of leg openings. A pant can be configured such that the pant has a closed waist and closed leg openings prior to being donned on the wearer, or the pant can be configured such that the waist is closed and the leg openings formed while on the wearer. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, rear waist fastened). Examples of suitable pants are disclosed in U.S. Pat. No. 5,246,433; U.S. Pat. No. 5,569,234; U.S. Pat. No. 6,120,487; U.S. Pat. No. 6,120,489; U.S. Pat. No. 4,940,464; U.S. Pat. No. 5,092,861; U.S. Pat. No. 5,897,545; U.S. Pat. No. 5,957,908; and U.S. Patent Publication No. 2003/0233082 A1.

Description:

In general humans can hear sounds at frequencies which range from about 20 Hz to about 20 kHz. However, human speech typically falls within a range of frequencies from about 2 kHz to about 5 kHz. So, the human ear can be particularly sensitive to noise intensities within the range of about 2 kHz to about 5 kHz. Also, the crackling sound discussed previously can fall within this frequency range.

Because the crackling sound can fall within the frequency range of about 2 kHz to about 5 kHz, the sound intensities in decibels within this frequency range are hereafter referred to as "crackling sound intensities". A film constructed in accordance with the present invention can exhibit reduced the crackling sound intensities within the frequency range above when the film is subjected to expected forces.

As shown in FIG. 1A, a non-elastic thermoplastic film 100 constructed in accordance with the present invention comprises a first surface 102, a second surface 104, and a noise abatement region 110. The first surface 102 is facing the viewer in FIG. 1A while the second surface 104 is disposed opposite of the first surface 102.

The non-elastic thermoplastic film 100 may further comprise, in some embodiments, a fastening component 119. The fastening component 119 may be disposed in any suitable location in the non-elastic thermoplastic film 100. For example, as shown, the fastening component 119 is disposed within the noise abatement region 110. As yet another example, the fastening component 119 can be completely surrounded by the noise abatement region 110. Other examples include where the noise abatement region 110 is disposed adjacent to one or more sides of the fastening component 119. The fastening component 119 can be positioned in any suitable location on the non-elastic thermoplastic film.

The fastening component 119 may comprise a portion of any suitable fastening system known in the art. For example, as shown, the fastening component 119 may comprise a slot member 120 having an inboard portion 164 and an outboard portion 166 which define a slot 122 therebetween. In some embodiments, the slot 122 may comprise a slit 136. As another example, the fastening component 119 may comprise a tab member which includes a tab element or a plurality of tab elements. Tab members, tab elements, slot members, and slots are described in U.S. Pat. No. 6,432,098 and U.S. Patent Application Publication No. 2003/0233082.

As shown, in some embodiments, the noise abatement region 110 may comprise a plurality of noise abatement elements 112. In some embodiments, the noise abatement region 110 may comprise only one noise abatement element 112. in some embodiments, the plurality of noise abatement elements 112 can be spaced apart by a first distance 140 which can be generally parallel to a first direction 199. The plurality of noise abatement elements 112 can be spaced apart by a second distance 150 which can be generally parallel to a second direction 198.

The first distance 140 and the second distance 150 between the noise abatement elements can be any suitable size. For example, in some embodiments, the first distance 140 and/or the second distance 150 can be between about 1 mm to about 10 mm or any individual number within the range. In some embodiments, the first distance 140 and/or the second distance 150 can be between about 3 mm to about 6 mm.

In some embodiments, the first direction 199 can be generally parallel to a machine direction. In some embodiments, the second direction 198 can be generally parallel to a cross machine direction. In some embodiments, the second direction 198 can be generally perpendicular to the first direction 199. In some embodiments, the second direction 199 can be generally parallel to a primary direction of a fastening force 1099 (shown in FIG. 4). In some embodiments, the fastening force 1099 (shown in FIG. 4) can be the expected forces when the non-elastic thermoplastic film 100 is in use. For example, where the non-elastic thermoplastic film 100 comprises a fastening member 120 and is used in a disposable absorbent article, the fastening force 1099 (shown in FIG. 4) can be those forces which are expected during fastening.

may comprise an area of between about 10 mm² to about 75 mm². In some embodiments, a noise abatement element 112 may comprise an area of between about 20 mm² to about 50 mm².

It has been discovered that the addition of a plurality of noise abatement elements 112 can reduce the level of crackling sound intensities (in decibels) exhibited by films at particular frequencies. It has also been discovered that films of different chemistries can have different noise intensities at particular frequencies. Data for varying chemistries of film and for flat versus films comprising noise abatement elements are provided in Table I. For the purposes of the present invention, a flat film does not comprise a noise abatement element as defined herein.

TABLE I

| Sample # | First distance 140 (mm) | Second distance 150 (mm) | length 145 (mm) | width 155 (mm) | 2000 Hz dBa | 2500 Hz dBa | 3150 Hz dBa | 4000 Hz dBa | 5000 Hz dBa |
|---|---|---|---|---|---|---|---|---|---|
| 1 | na | na | na | na | 76.4 | 78.6 | 78.3 | 78.8 | 79.3 |
| 2 | 3 | 3 | 3 | 3 | 63.4 | 65.6 | 66.2 | 60.1 | 56.7 |
| 3 | na | na | na | na | 67.6 | 69.5 | 72.3 | 70 | 70 |
| 4 | 3 | 3 | 3 | 3 | 57.5 | 65.7 | 63.6 | 57.8 | 52 |

The noise abatement elements 112, in some embodiments, may comprise apertures. As shown, in some embodiments, the noise abatement elements 112 can have a square shape. However, the noise abatement elements 112 of the present invention may comprise any suitable shape known in the art. Some examples of suitable shapes include circular, triangular, elliptical, a trapezoidal, a rhomboidal, or any polygonal shape. Embodiments where the plurality of noise abatement elements 112 comprise slits are contemplated.

As shown in FIG. 1B, in some embodiments, the plurality of the noise abatement elements 112 of the non-elastic thermoplastic film 100 can have a length 145 which can be generally parallel to the first direction 199. In some embodiments, the plurality of noise abatement elements 112 can have a width 155 which can be generally parallel to the second direction 198.

The noise abatement elements 112 can be of any suitable length, and the noise abatement elements 112 can be of any suitable width. For example, in some embodiments, the length 145 and/or the width 155 of a noise abatement element 112 can be between about 1 mm to about 10 mm or any individual number within the range. In some embodiments, the length 145 and/or width 155 can be between about 3 mm to about 6 mm. In some embodiments, at least one noise abatement element 112 has a length within the range specified above while another noise abatement element 112 has a different length. In some embodiments, at least one noise abatement element 112 has a width within the range specified above while another noise abatement element 112 has a different width.

The width 155 can be greater than the length 145 in some embodiments. In some embodiments, the length 145 can be greater than the width 155. In some embodiments, the length 145 can be equal to the width 155.

The noise abatement elements 112 may comprise any suitable area. For example, in some embodiments, a noise abatement element 112 may comprise an area of between about 1 mm² to about 100 mm² or any individual number within the range. In some embodiments, a noise abatement element 112

Samples 1 and 2 were made from poly(ethylene teraphthalate). Sample 1 did not comprise any noise abatement elements while sample 2 comprised a plurality of noise abatement elements. The noise abatement elements had a length of about 3 mm and a width of about 3 mm. The noise abatement elements were separated by a first distance which was about 3 mm and a second distance which was about 3 mm. As shown in Table I, the noise abatement elements provided reduced noise intensities in all frequencies tested.

Samples 3 and 4 were made from a low density polyethylene. Sample 3 did not comprise any noise abatement elements while sample 4 comprised a plurality of noise abatement elements. The noise abatement elements had a length of about 3 mm and a width of about 3 mm. The noise abatement elements were separated by a first distance which was about 3 mm and a second distance which was about 3 mm. As shown in Table I, the noise abatement elements provided reduced noise intensities for all frequencies tested. Note also that the low density polyethylene films exhibited reduced crackling sound intensities at the frequencies tested than did the poly(ethylene teraphthalate) films.

Based on the data, films comprising noise abatement elements can provide reduced crackling sound intensities over a flat film. Furthermore, the chemistry of the film can impact the crackling sound intensities exhibited by the film.

It has also been discovered that the length 145, the width 155, the first distance 150, and the second distance 140, can impact the crackling sound intensities which a non-elastic thermoplastic film 100 will exhibit. Data for varying lengths 145, widths 155, first distances 150, and second distances 140, are provided in Table II.

Table II provides crackling sound intensities in decibels at varying frequencies for several exemplary embodiments of the present invention. The exemplary embodiments vary with regard to the first distance 140 and the second distance 150 between the noise abatement elements 112. Also, the exemplary embodiments provided in Table II vary with regard to the length 145 and width 155 of the noise abatement elements 112.

All samples were constructed from a polypropylene copolymer film. Also all samples comprised a slot member similar to the non-elastic thermoplastic film shown in FIG. 1A. Note that a flat polypropylene copolymer film was not tested; however, it is believed that the crackling sound intensities of a flat polypropylene film versus the crackling sound intensities of the exemplary embodiments below would follow the trend as shown in Table I.

the noise abatement region 110 may include a higher number of noise abatement elements 112 which are aligned generally parallel to the second direction 198 (shown in FIGS. 1A and 1B) as opposed to the first direction 199 (shown in FIGS. 1A and 1B). In other embodiments, the noise abatement region 110 may include a higher number of noise abatement elements 112 which are aligned generally parallel to the first direction 199 (shown in FIGS. 1A and 1B) as opposed to the

TABLE II

| Sample No. | First distance 140 (mm) | Second distance 150 (mm) | length 145 (mm) | width 155 (mm) | Open Ratio | 2000 Hz dBa | 2500 Hz dBa | 3150 Hz dBa | 4000 Hz dBa | 5000 Hz dBa |
|---|---|---|---|---|---|---|---|---|---|---|
| 5 | 3 | 3 | 6 | 6 | 0.44 | 59 | 65.2 | 66 | 59.7 | 53.5 |
| 6 | 6 | 6 | 6 | 6 | 0.25 | 65.5 | 68.9 | 72.6 | 70.5 | 71.2 |
| 7 | 6 | 3 | 6 | 3 | 0.25 | 65 | 68.9 | 72.1 | 73.3 | 71.7 |
| 8 | 3 | 3 | 3 | 3 | 0.25 | 61.9 | 66 | 67.9 | 65.9 | 65.7 |
| 9 | 3 | 6 | 3 | 6 | 0.25 | 61.2 | 64.7 | 66.8 | 61.5 | 64.7 |
| 10 | 3 | 6 | 6 | 3 | 0.22 | 63.9 | 67.1 | 71.8 | 68.8 | 70.4 |
| 11 | 6 | 3 | 3 | 6 | 0.22 | 61.9 | 64.5 | 66.5 | 60.4 | 56.5 |
| 12 | 6 | 6 | 3 | 3 | 0.11 | 68.4 | 70.6 | 72.2 | 74.1 | 71.1 |

As shown in Table II, sample number 5, having the highest open area ratio exhibited the lowest crackling sound intensities at the frequencies tested. However, a film having a higher amount of open area may not exhibit reduced crackling sound intensities when compared to a film having a lower amount of open area. For example, comparing samples 6 and 10, a film having a lower open ratio can, in some embodiments, exhibit reduced crackling sound intensities over a film having a higher open area.

The open area of the non-elastic thermoplastic film 100 of the present invention can be any suitable percentage of the area of the non-elastic thermoplastic film 100. For example, in some embodiments, the open area can be in a range from about 5% to about 90% or any individual number within the range. In other embodiments, the open area of the non-elastic thermoplastic film 100 can be in a range from about 10% to about 70%. In yet other embodiments, the open area of the non-elastic thermoplastic film 100 can be in a range from about 10% to about 60%. In yet other embodiments, the open area of the non-elastic thermoplastic film 100 can be in a range from about 11% to about 44%.

The number of the noise abatement elements 112 aligned in a particular direction may affect the crackling sound intensities exhibited by the non-elastic thermoplastic film 100. For example, where the fastening force 1099 (shown in FIG. 4) is generally parallel to the second direction 198 (shown in FIGS. 1A and 1B), a higher number of noise abatement elements 112 aligned parallel to the second direction 198 (shown in FIGS. 1A and 1B) may allow the non-elastic thermoplastic film 100 to exhibit reduced crackling sound intensities over a non-elastic thermoplastic film 100 having a smaller number of noise abatement elements 112 aligned in the second direction 198 (shown in FIGS. 1A and 1B). In some embodiments, second direction 198 (shown in FIGS. 1A and 1B). In other embodiments, the noise abatement region 110 may include an increased number of noise abatement elements 112 which are aligned generally parallel to the primary direction of an applied fastening force 1099 (shown in FIG. 4).

It has also been discovered that a thickness of a non-elastic thermoplastic film can impact the crackling sound intensities exhibited by the non-elastic film at particular frequencies. Data pertaining to the crackling sound intensities of films comprising noise abatement elements having varying thicknesses are provided in Table III.

Samples 8 and 13 comprised polypropylene copolymer films having noise abatement elements. The noise abatement elements for both samples 8 and 13 were similarly configured. However, sample 8 had a thickness of about 101.6 μm while sample 13 had a thickness of about 50.8 μm. The data for sample 8 in Table II was used in Table III.

TABLE III

| Sample No. | First distance 140 (mm) | Second distance 150 (mm) | length 145 (mm) | width 155 (mm) | Open Ratio | 2000 Hz dBa | 2500 Hz dBa | 3150 Hz dBa | 4000 Hz dBa | 5000 Hz dBa |
|---|---|---|---|---|---|---|---|---|---|---|
| 8 | 3 | 3 | 3 | 3 | 0.25 | 61.9 | 66 | 67.9 | 65.9 | 65.7 |
| 13 | 3 | 3 | 3 | 3 | 0.25 | 61.3 | 67.6 | 70.6 | 69.6 | 72.8 |

As shown in Table III, sample 13 (the thinner film sample) exhibited higher crackling sound intensities at some of the measured frequencies. Based on the data, thicker films can provide some noise abatement qualities; however, thicker films can be more expensive. An advantage of the present invention is that thinner films constructed in accordance with the present invention may exhibit crackling sound intensities which are reduced from or similar to their thicker flat film counterparts. So, utilization of the films of the present invention may allow for decreased costs.

In some embodiments, a reduction in crackling sound intensities may comprise at least a 1% decrease in decibels at a frequency tested. In some embodiments, a reduction in crackling sound intensities may comprise at least a 1% decrease in decibels at all frequencies tested, i.e. 2 kHz, 2.5 kHz, 3.1 kHz, 4 kHz, and 5 kHz.

As stated previously, in some embodiments, the plurality of noise abatement elements 112 may comprise apertures. As shown in FIG. 2A, in some embodiments, the apertures 212 may extend through a thickness 210 of the non-elastic thermoplastic film 100. In some embodiments, the thickness 210 of the non-elastic thermoplastic film 100 can be in a range of about 0.01 µm to about 110 µm or any individual number within the range. In other embodiments, the thickness 210 can be in a range from about 50 µm to about 110 µm. The non-elastic thermoplastic film 100 can be of any suitable thickness 210.

As shown in FIG. 2B, the apertures 212 may extend only partially through the thickness 210 of the non-elastic thermoplastic film 100. For example, the apertures 212 may extend through the first surface 102 of the non-elastic thermoplastic film 100 but only partially extend through the thickness 210 of the non-elastic thermoplastic film 100. The apertures 212 can have a depth 230 which can vary. For example, in some embodiments, the depth 230 can be in a range of about 5% of the thickness 210 to about 99% of the thickness 210 of the non-elastic thermoplastic film 100 or any individual number within the range. In some embodiments, the depth 230 can be in a range of between about 10% to about 75% of the thickness 210 of the non-elastic thermoplastic film 100. In some embodiments, the depth 230 can be in a range of between about 25% and 50% of the thickness 210 of the non-elastic thermoplastic film 100.

In some embodiments, the apertures 212 can extend through the second surface 104 but only extend partially through the thickness 210 of the non-elastic thermoplastic film 100. In some embodiments, at least one aperture 212 can extend through the first surface 102 but only partially through the thickness 210, and at least one aperture 212 can extend through the second surface 104 but only partially through the thickness 210 of the non-elastic thermoplastic film 100.

Embodiments where the plurality of noise abatement elements 112 include slits are contemplated. Slits are described in U.S. Pat. No. 6,432,098 and in U.S. Patent Application Publication No. 2002/0103470. Embodiments where the plurality of noise abatement elements 112 includes at least one aperture which extends through both the thickness 210 of the non-elastic thermoplastic film 100, at least one noise abatement element 112 having a depth 230 which is a percentage of the thickness 210, and/or at least one slit are contemplated.

The non-elastic thermoplastic film 100 may be made up of many different thermoplastic polymers. For example the non-elastic thermoplastic film 100 may comprise at least one of polyurethanes, polyolefins (e.g., polypropylenes, polyethylenes, etc.), polystyrenes, polycarbonates, polyesters, polymethacrylates, ethylene vinyl acetate copolymers, ethylene vinyl alcohol copolymers, polyvinylchlorides, acrylate modified ethylene vinyl acetate polymers, ethylene acrylic acid copolymers, nylons, fluorocarbons, the like, or any combination thereof. Suitable thermoplastic polymers will generally have a melt flow index of 5-200 grams/10 minutes measured at the appropriate conditions for the polymer as specified in ASTM D 1238.

Figure 3A:
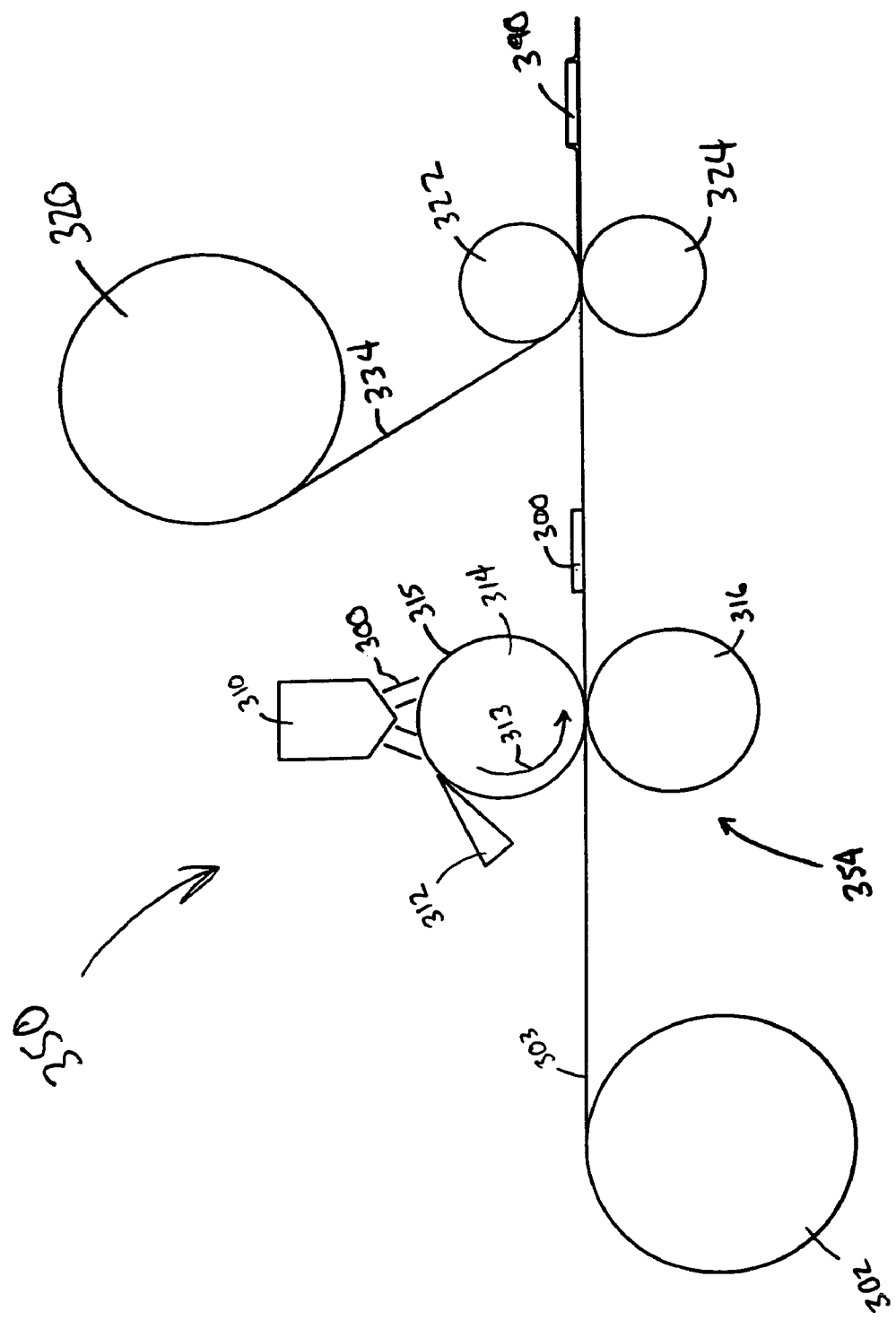
FIG. 3A is a schematic view showing an embodiment a suitable apparatus for making the non-elastic thermoplastic film of FIG. 1A.

Non-elastic thermoplastic films constructed in accordance with the present invention can be made via various processes. For example, in some embodiments, the non-elastic thermoplastic films can be at least partially impregnated into one or more fibrous substrates. Some suitable examples of the impregnation process, include spraying, coating, screen-printing, intaglio printing, flexographic printing, ink jet printing, and the like, onto a fibrous substrate. In some embodiments the non-elastic thermoplastic film can be at least partially impregnated into a fibrous substrate via a rotogravure printing process as shown in FIG. 3A. The rotogravure printing process can provide flexibility in desired x-y-z dimensions of the non-elastic thermoplastic film and desired quantity of deposition of the molten thermoplastic resin. Examples of other suitable processes and control methodologies are discussed in U.S. Patent Application Publication No. 2003/0084996; U.S. Patent Application Publication No. 2004/0178544; and U.S. Patent Application Publication No. 2003/0088220.

As shown in FIG. 3A, in some embodiments, a composite material 390 including the non-elastic thermoplastic film of the present invention can be produced via a rotogravure printing process 350. A fibrous substrate 303, which can be provided by a supply roll 302, can move through a rotogravure printing device 354. The rotogravure printing device 354 can deposit molten thermoplastic material 300 onto the fibrous substrate 303 to at least partially impregnate the fibrous substrate 303.

The rotogravure printing device 354 may comprise a transfer roll 314, an anvil roll 316, a delivery apparatus 310, and a doctor blade 312. A delivery apparatus 310 can provide the transfer roll 314 with a molten thermoplastic material 300. In this process, the molten thermoplastic material 300 is delivered to one or more depressions formed in an exterior surface 315 of the transfer roll 314. The exterior surface 315 of the transfer roll 314 and the one or more depressions therein, are discussed further in regard to FIG. 3B.

As the transfer roll 314 rotates in a direction indicated by arrow 313, the doctor blade 312 can scrape off excess molten thermoplastic material 300 from the exterior surface 315 of the transfer roll 314. In order to facilitate the removal of the non-elastic thermoplastic film from the transfer roll 314, the doctor blade 312 can be configured such that some of the molten thermoplastic material 300 remains on the exterior surface 315 of the transfer roll 314. The molten thermoplastic material 300 without the fibrous substrates 303 and 334 can be the non-elastic thermoplastic film of the present invention.

The transfer roll 314 can continue to rotate, thereby causing the one or more depressions and the molten thermoplastic material 300 which they contain to come into contact with fibrous substrate 303 against the anvil roll 316. At this point the molten thermoplastic material 300 can be partially impregnated onto the fibrous substrate 303. The fibrous substrate 303 can be advanced by the transfer roll 314 and the anvil roll 316 to downstream processes.

Optionally, a second fibrous substrate 334, which can be provided by a supply roll 320, can be combined with the substrate 303 to cover the molten thermoplastic material 300. The molten thermoplastic material 300 can partially impregnate into the second fibrous substrate 334 to form a composite material 390.

The degree of impregnation of both substrates 303 and 334 by the molten thermoplastic material 300 can be controlled by applying a desired pressure onto the composite material 390 to effect the impregnation. For example, as shown, a pair of nip rolls 322 and 324 can apply a predetermined pressure to affect a desired amount of impregnation. Additionally, the nip rolls 322 and 324 can be heated or chilled which also can impact the amount of impregnation of a thermoplastic material into the fibrous substrates. Pressure can be applied to the fibrous substrate by any suitable means known in the art including contacting or non-contacting means. The degree of impregnation can also be affected by the viscosity of the molten thermoplastic material 300, the porosity of the fibrous substrates 303 and 334, and the surface tension of both the molten thermoplastic material 300 and the fibrous substrates 303 and 334.

The delivery apparatus 310 can be any suitable apparatus for delivering molten thermoplastic material 300 to the transfer roll 314. Some suitable examples of delivery apparatuses include a trough, an extruder, a gear pump, the like, or any combination thereof. Similarly, the rotogravure-printing device 354 can be any suitable conventional thermal rotogravure device. An example of a suitable rotogravure-printing device can be obtained from Roto-Therm Inc. of California.

Figure 3B:
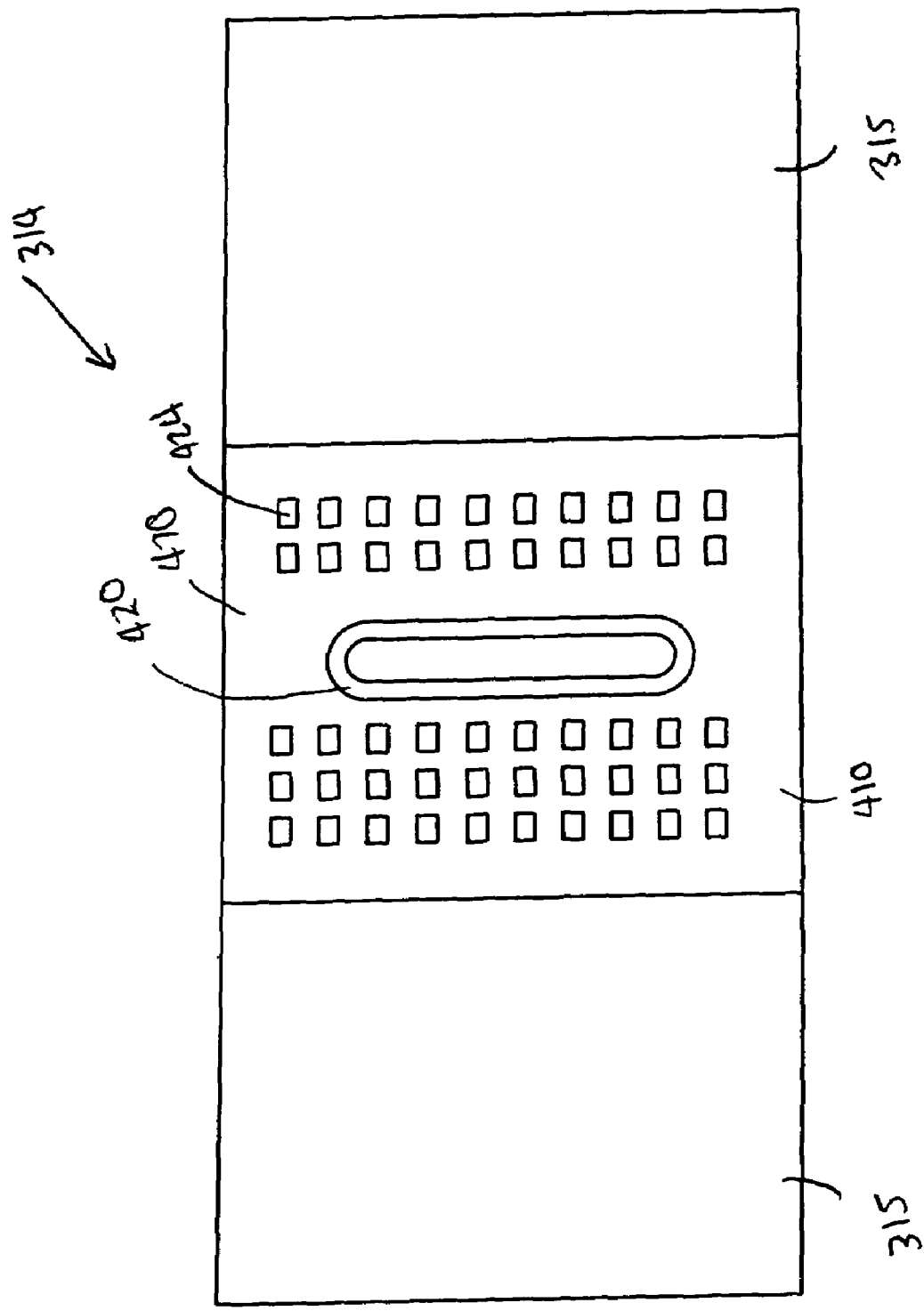
FIG. 3B is an elevation view of a transfer roll of the apparatus of FIG. 3A.

As shown in FIG. 3B the exterior surface 315 of the transfer roll 314 may comprise a depression 470 which can produce a non-elastic thermoplastic film in accordance with the present invention. The depression 470 formed in the exterior surface 315 of the transfer roll 314 can receive a portion of the molten thermoplastic material 300 (shown in FIG. 3A) when the molten thermoplastic material 300 (shown in FIG. 3A) is deposited on the exterior surface 315 of the transfer roll 314.

In some embodiments, where the non-elastic thermoplastic film comprises a slot member 120 (shown in FIG. 1A), the depression 470 may comprise a first surface 410 and a second surface 420. The first surface 410 and the second surface 420 can be submerged under the molten thermoplastic material 300 (shown in FIG. 3A) when the depression 470 is at least partially filled. The first surface 410 can correspond to the noise abatement region 110 (shown in FIGS. 1A and 1B) of the resulting non-elastic thermoplastic film. The second surface 420 may correspond to the slot member 120 (shown in FIG. 1A) of the resulting non-elastic thermoplastic film.

The first surface 410 and the second surface 420 of the depression 470 can be at equal depths from the exterior surface 315 of the transfer roll 314; however, they are not required to be. For example, in some embodiments, the first surface 410 can be nearer to the exterior surface 315 of the transfer roll 314 such that the noise abatement region 110 (shown in FIGS. 1A and 1B) is thinner than the slot member 120 (shown in FIG. 1A) of the resulting non-elastic thermoplastic film. In other embodiments, the second surface 420 can be nearer to the exterior surface 315 of the transfer roll 314 such that the slot member 120 (shown in FIG. 1A) is thinner than the noise abatement region 110 (shown in FIGS. 1A and 1B) of the resulting non-elastic thermoplastic film.

The slot member 120 (shown in FIG. 1A) can have any suitable thickness. For example, the thickness of the slot member 120 (shown in FIG. 1A) can be determined based on the expected in use forces for the slot member 120 (shown in FIG. 1A). In some embodiments, the slot member 120 (shown in FIG. 1A) can have a thickness which is at least about 0.5 mm.

The depression 470 may further include a third surface 424 which may correspond to the noise abatement elements 112 (shown in FIGS. 1A, 1B, 2A, and 2B). In some embodiments, the third surface 424 is not submerged under the molten thermoplastic material (shown in FIG. 3A) when the depression 470 is at least partially filled such that the resulting the non-elastic thermoplastic film comprises apertures 212 (shown in FIGS. 2A and 2B) which extend through the thickness 210 (shown in FIGS. 2A and 2B) of the non-elastic thermoplastic film. In other embodiments, the third surface 424 can be submerged under the molten thermoplastic material 300 (shown in FIG. 3A) when the depression 470 is at least partially filled such that the resulting non-elastic thermoplastic film comprises apertures 212 (shown in FIGS. 2A and 2B) which do not extend through both the entire thickness 210 (shown in FIGS. 2A and 2B) of the resulting non-elastic thermoplastic film. In yet other embodiments, the third surface 424 can vary such that the resulting non-elastic thermoplastic film has at least one aperture 212 (shown in FIGS. 2A and 2B) which extends through the thickness 210 (shown in FIGS. 2A and 2B) of the resulting non-elastic thermoplastic film and at least one aperture 212 (shown in FIG. 2A and 2B) which does not extend through both the entire thickness 210 (shown in FIG. 2A and 2B) of the resulting non-elastic thermoplastic film.

A non-elastic thermoplastic film constructed in accordance with the present invention may be incorporated into a number of articles for which reduced noise levels are desired. For example, a non-elastic thermoplastic film constructed in accordance with the present invention can be incorporated into a disposable absorbent article such as a diaper, training pants, sanitary napkins, belts, bibs, wraps, and the like. Additionally, the non-elastic thermoplastic film can be utilized in any suitable location within the article. For example, the non-elastic thermoplastic film can be utilized in a side panel of a diaper. Articles which may utilize the non-elastic thermoplastic film of the present invention are discussed in U.S. Pat. No. 6,432,098; U.S. Patent Application Publication No. 2003/0233082; and U.S. Patent Application Publication No. 2004/0225273.

Figure 4:
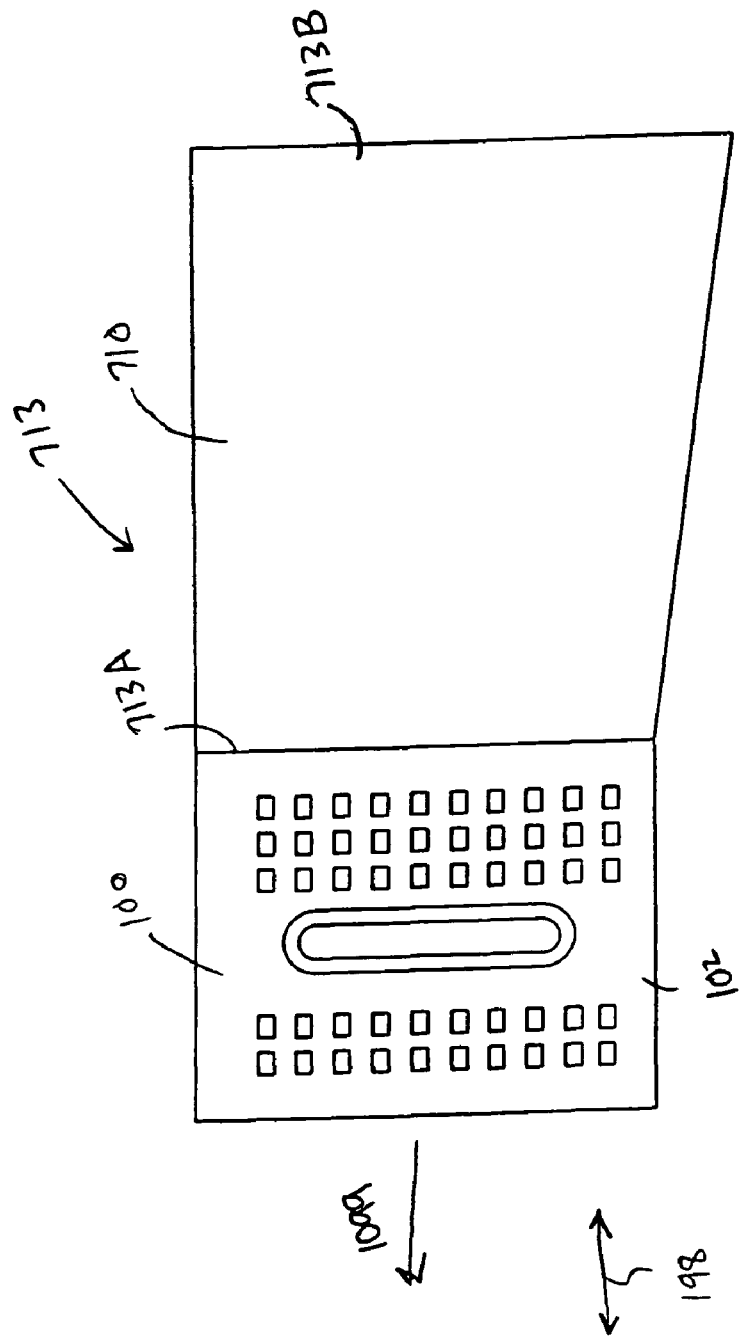
FIG. 4 is a plan view showing a side panel comprising the non-elastic thermoplastic film of FIG. 1A.

FIG. 4 shows an exemplary embodiment of the non-elastic thermoplastic film 100 constructed in accordance with the present invention incorporated into a side panel 713. As shown, the side panel 713 may comprise the non-elastic thermoplastic film 100 and a panel region 710. In some embodiments, the non-elastic thermoplastic film 100 can be attached adjacent to an outboard end 713A of the side panel 713. An inboard end 713B of the side panel 713 can be attached to a disposable absorbent article 720 (shown in FIG. 5). As shown, the first surface 102 of the non-elastic thermoplastic film 100 is exposed to the viewer; however, in some embodiments, the first surface 102 and/or a second surface (not shown) of the non-elastic thermoplastic film 100 can be covered by a fibrous substrate, e.g. a nonwoven. The non-elastic thermoplastic film 100 can be joined to the fibrous substrate by any suitable means known in the art. Suitable examples of joining means include adhesive bonding, thermal bonding, compression bonding, mechanical bonding, fusion bonding, the like, or any combination thereof. In some embodiments, the panel region 710 can be elastically extensible. In some embodiments, the panel region 710 can be extensible but not elastically extensible.

As discussed previously, fastening force 1099 can be applied to the side panel 713 during fastening. As shown, in some embodiments, the fastening force 1099 can be generally parallel to the second direction 198. In some embodiments, the fastening force 1099 may comprise multiple force components of which the primary force component act in a direction generally parallel to the second direction 198.

Figure 5:
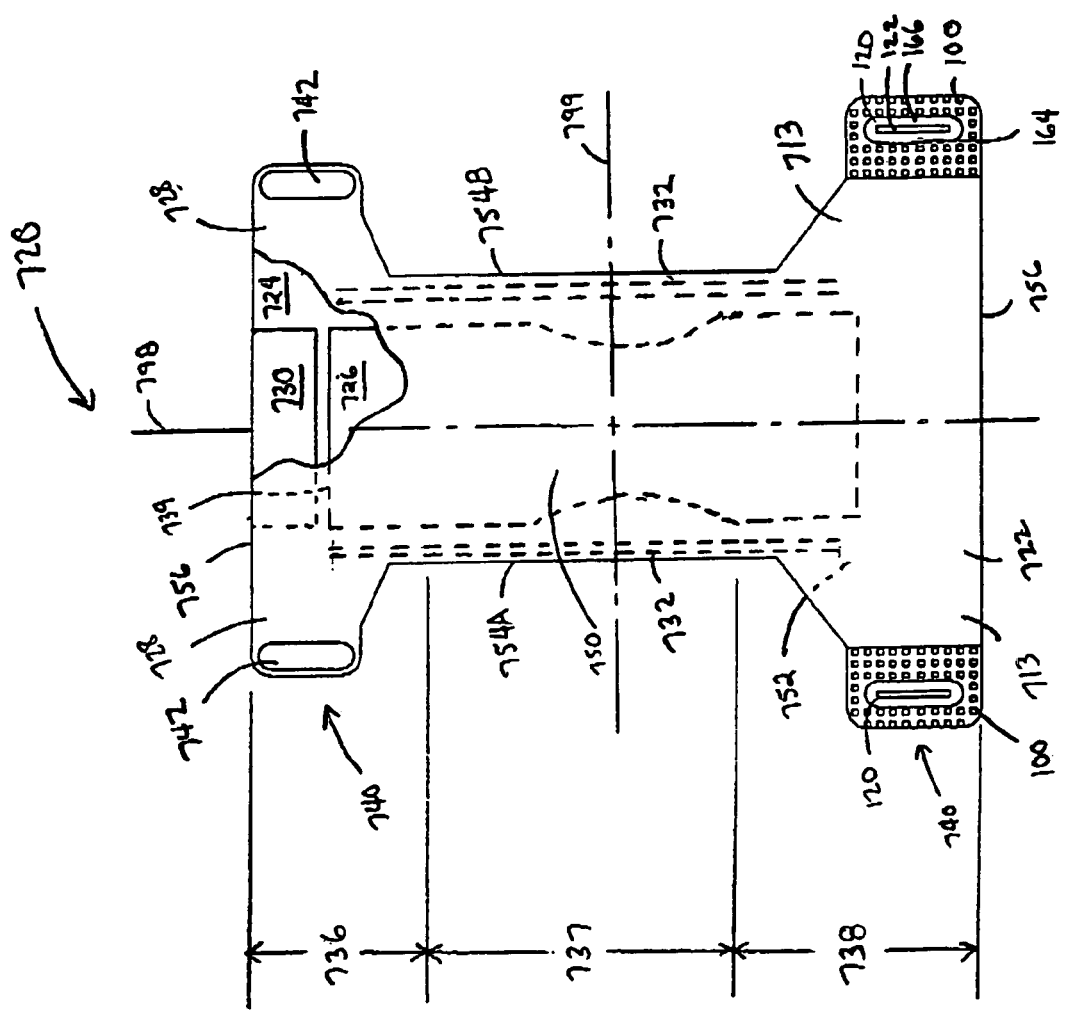
FIG. 5 is a plan view of a disposable absorbent article comprising the side panel of FIG. 4.

As shown FIG. 5, a non-elastic thermoplastic film 100 of the present invention can be utilized in a disposable absorbent article such as a diaper 720. As shown, the diaper 720 is in its flat-out, uncontracted state (i. e., with elastic induced contraction pulled out) with portions of the structure being cut-away to more clearly show the construction of the diaper 720. The portion of the diaper 720 which faces or contacts the wearer, the inner surface 750, is oriented towards the viewer. The diaper 720 may comprise a liquid pervious topsheet 722 and a backsheet 724 attached to at least a portion of the topsheet 722. The diaper 720 further comprises an absorbent core 726 positioned between the topsheet 722 and the backsheet 724. The diaper 720 may further comprise leg cuffs 732 and a waist feature 730.

The diaper 720 is shown in FIG. 5 to have an outer surface 752 opposed to the inner surface 750, a first waist region 736, a second waist region 738 opposed to the first waist region 736, a crotch region 737 positioned between the first waist region 736 and the second waist region 738. The diaper 720 also has a first longitudinal edge 754A, a second longitudinal edge 754B and waist edges 756. The longitudinal edges 754A and 754B run generally parallel to a longitudinal centerline 798, and the waist edges 756 run generally parallel to a lateral centerline 799.

The waist feature 730 can help provide improved fit and containment of the diaper 720 about a wearer. The waist feature 730 is that portion or zone of the diaper 720 which is intended to elastically expand and contract to dynamically fit the wearer's waist. The elastic waist feature 730 generally extends longitudinally outward from at least one of the waist edges 739 of the absorbent core 726 and generally forms at least a portion of the waist edge 756 of the diaper 720. The elastic waist feature 730 or any of its constituent elements can include a separate element affixed to the diaper 720, the elastic waist feature 730 can be constructed as an extension of other elements of the diaper 720 such as the backsheet 724, the topsheet 722 or both the backsheet 724 and the topsheet 722. Examples of suitable waist features include those described in U.S. Pat. No. 4,515,595, U.S. Pat. No. 5,151,092, and U.S. Pat. No. 5,221,274. Although disposable diapers are generally constructed so as to have two elastic waist features, one positioned in a first waist region and one positioned in a second waist region, diapers can be constructed with a single elastic waist feature as shown in FIG. 5.

The diaper 720 further comprises a first pair of side panels 728 which extend outward from the first longitudinal edge 754A and the second longitudinal edge 754B in the first waist region 736. Similarly, the diaper 720 further comprises a second pair of side panels 713 which extend outward from the first longitudinal edge 754A and the second longitudinal edge 754B in the second waist region 738.

The diaper 720 further comprises a fastening system 740 which joins at least a portion of the first waist region 736 with at least a portion of the second waist region 738, preferably to form leg and waist openings. The fastening system 740 can also work with the waist feature(s) 730 to maintain lateral tension in order to keep the diaper 720 in place about the waist of the wearer. The fastening system 740 may be the primary fastening system for joining the first and second waist regions 736 and 738. However, the fastening system 740 may be used alone or in conjunction with other fastening means such as hook and loop fasteners, hook and hook fasteners, tape fasteners, snaps, buttons, and the like to provide different fastening characteristics. For example, the fastening system 740 may provide the diaper 720 with a disposal means for fastening the diaper 720 in a configuration convenient for disposal. Further, secondary fastening means may provide the diaper 720 with a means for adjusting fit or may increase the strength of the connection between the first waist region 736 and the second waist region 738. As shown, in some embodiments, the fastening system 740 can be included on the first pair of side panels 728 and the second pair of side panels 713.

In some embodiments, the fastening system 740 may comprise a tab and slot fastening system. For example, each of the second pair of side panels 713 may comprise the non-elastic thermoplastic film 100 of the present invention which includes the slot member 120. The slot member 120 can have an inboard portion 164, an outboard portion 166, and a slot 122 therebetween. Additionally, each of the second pair of side panels 728 may comprise a tab element 742. The tab elements 742 can be adaptable to pass through the slots 122 and engage the outboard portion 166 of the slot member 120, thereby fastening the first waist region 736 to the second waist region 738. Embodiments where the fastening system 740 includes a plurality of slot members are contemplated.

The fastening system 740 can be prefastened such that a caregiver or wearer may pull on the diaper 720 when removed from a package. Alternatively, the fastening system 740 can be unfastened in the package such that the caregiver or wearer fastens the fastening system 740 while donning the diaper 720. In yet another embodiment, a package may comprise both prefastened and unfastened diapers 720 for the convenience of the caregiver or the wearer. In yet another embodiment, a portion of the fastening system 740 can be prefastened such that the wearer or caregiver fastens the remaining portion of the fastening system 740 to don the article on the wearer.

In some embodiments, the first pair of side panels 728 in conjunction with the second pair of side panels 713 can form a portion of the leg openings when the diaper 720 is fastened. The first pair of side panels 728 and/or the second pair of side panels 713 can form a portion of the leg openings which would be disposed on an outer surface of a leg of a wearer. A crotch region of the diaper 737 in conjunction with the first waist region 736 and the second waist region 738 can form a portion of the leg openings which would be disposed on an inner surface of the leg of the wearer.

The topsheet 722 and the backsheet 724 can have length and width dimensions generally larger than those of the absorbent core 726. The topsheet 722 and the backsheet 724 can extend beyond the edges of the absorbent core 726, thereby forming the periphery of the diaper 720. While the topsheet 722, the backsheet 724, and the absorbent core 726 may include many different materials and may be assembled in a variety of well known configurations, preferred diaper materials and configurations are described generally in U.S. Pat. No. 3,860,003 and U.S. Pat. No. 5,151,092.

Some examples of suitable topsheets are described further in U.S. Pat. No. 3,929,135; U.S. Pat. No. 4,324,246; U.S. Pat. No. 4,342,314; U.S. Pat. No. 4,463,045; U.S. Pat. No. 5,006,394; U.S. Pat. No. 4,609,518; U.S. Pat. No. 4,629,643. Any portion of the topsheet may be coated with a lotion as is known in the art. Examples of suitable lotions include those described in U.S. Pat. No. 5,607,760; U.S. Pat. No. 5,609,587; U.S. Pat. No. 5,635,191; U.S. Pat. No. 5,643,588; U.S. Pat. No. 5,968,025; U.S. Pat. No. 6,716,441; and PCT Publication No. WO 95/24173.

Further, the topsheet may be fully or partially elasticated or may be foreshortened so as to provide a void space between the topsheet and the absorbent core. Exemplary structures including elasticized or foreshortened topsheets are described in more detail in U.S. Pat. No. 4,892,536; U.S. Pat. No. 4,990,147; U.S. Pat. No. 5,037,416; and U.S. Pat. No. 5,269,775.

A suitable backsheet for use in the disposable absorbent article of the present invention may be impervious to liquids (e.g., urine) and comprise a thin plastic film such as a thermoplastic film having a thickness, for example, of about 0.012 mm (0.5 mil) to about 0.051 mm (2.0 mils). Suitable backsheet films include those manufactured by Tredegar Corporation, based in Richmond, Va., and sold under the trade name CPC2 film. Other suitable backsheet materials may include breathable materials which permit vapors to escape from the pull-on garment while still preventing exudates from passing through the backsheet. Suitable breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746; U.S. Pat. No. 5,938,648; U.S. Pat. No. 5,865,823; and U.S. Pat. No. 5,571,096.

The backsheet, or any portion thereof, may be elastically extensible in one or more directions. In one embodiment, the backsheet may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801. In alternate embodiments, the backsheet may comprise elastic films, foams, strands, or combinations of these or other suitable materials with nonwovens or synthetic films.

A suitable absorbent core for use in the present invention may comprise any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure (s) may have varying caliper zones, hydrophilic gradient(s), a superabsorbent gradient(s), or lower average density and lower average basis weight acquisition zones; or may comprise one or more layers or structures). Suitable absorbent structures for use as the absorbent core are described in U.S. Pat. No. 4,610,678; U.S. Pat. No. 4,673,402; U.S. Pat. No. 4,834,735; U.S. Pat. No. 4,888,231; U.S. Pat. No. 5,137,537; U.S. Pat. No. 5,147,345; U.S. Pat. No. 5,342,338; U.S. Pat. No. 5,260,345; U.S. Pat. No. 5,387,207; and U.S. Pat. No. 5,625,222.

The backsheet may be attached to the topsheet, the absorbent core, or any other element of the disposable absorbent article by any attachment means known in the art. For example, the attachment means may include a uniform continuous layer of adhesive, a patterned layer of adhesive, or an array of separate lines, spirals, or spots of adhesive. Some suitable attachment means are disclosed in U.S. Pat. No. 4,573,986; U.S. Pat. No. 3,911,173; U.S. Pat. No. 4,785,996; and U.S. Pat. No. 4,842,666. Examples of suitable adhesives are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

Various sublayers may be disposed between the topsheet and the backsheet. The sublayer may be any material or structure capable of accepting, storing or immobilizing bodily exudates. Thus, the sublayer may include a single material or a number of materials operatively associated with each other. Further, the sublayer may be integral with another element of the pull-on garment or may be one or more separate elements attached directly or indirectly with one or more elements of the disposable absorbent article. Further, the sublayer may include a structure that is separate from the absorbent core or may include or be part of at least a portion of the absorbent core.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and, more specifically, having pores greater than about 1.0 mm in diameter.) One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. No. 6,680,422 and U.S. Pat. No. 5,941,864. Further, the sublayer, or any portion thereof, may include or be coated with a lotion or other known substances to add, enhance or change the performance or other characteristics of the element.

Embodiments of the present invention may include acquisition layers and dusting layers, each of which are well known in the art. Acquisition layer are further discussed in U.S. Pat. No. 5,460,622. Dusting layers are further discussed in U.S. Pat. No. 4,888,231.

The diaper 720 preferably further comprises leg cuffs 732 to improve containment of liquids and other body exudates. Each elasticized leg cuff 732 may include several different embodiments for reducing the leakage of body exudates in the leg regions. Some exemplary embodiments of leg cuffs are described in U.S. Pat. No. 3,860,003; U.S. Pat. No. 4,909,803; and U.S. Pat. No. 4,695,278.

Embodiments of the present invention may also include pockets for receiving and containing waste, spacers which provide voids for waste, barriers for limiting the movement of waste in the article, compartments or voids which accept and contain waste materials deposited in the pull-on garment, and the like, or any combinations thereof. Examples of pockets and spacers for use in absorbent products are described in U.S. Pat. No. 5,514,121; U.S. Pat. No. 5,171,236; U.S. Pat. No. 5,397,318; U.S. Pat. No. 5,540,671; U.S. Pat. No. 6,168,584; U.S. Pat. No. 5,306,266; and U.S. Pat. No. 5,997,520. Examples of compartments or voids in an absorbent article are disclosed in U.S. Pat. No. 4,968,312; U.S. Pat. No. 4,990,147; U.S. Pat. No. 5,062,840; and U.S. Pat. No. 5,269,755. Examples of suitable transverse barriers are described in U.S. Pat. No. 5,554,142; PCT Patent WO 94/14395; and U.S. Pat. No. 5,653,703. Examples of other structures suitable for management of low viscosity feces are disclosed in U.S. Pat. No. 5,941,864; U.S. Pat. No. 5,977,430; and U.S. Pat. No. 6,013,063.

Test Methods:

Sound Level Measurement

All measures to be carried out in temperature and humidity controlled conditions. Temperature is to be 22° C.+/−2° C. Relative Humidity is to be 50%+/−10%. All samples are to be held at these conditions for 24 hours prior to testing to allow them to equilibrate to the conditions.

Figure 6:
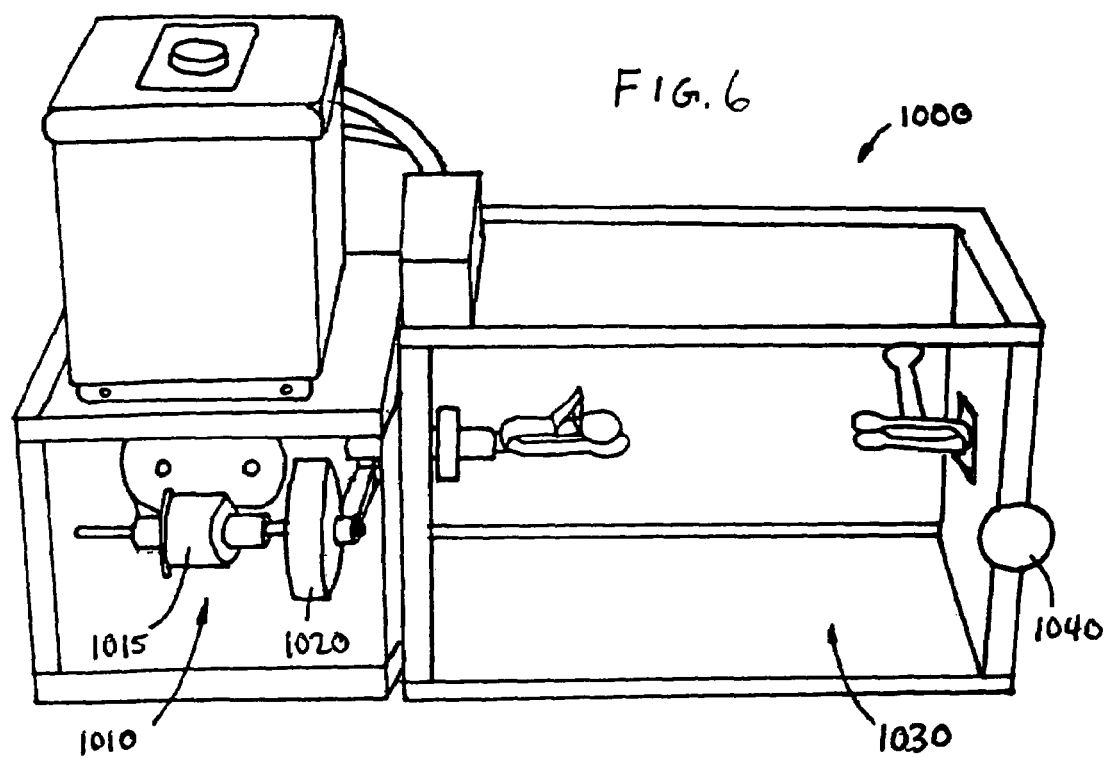
FIG. 6 is a front perspective view showing an apparatus used to measure sound levels generated by non-elastic thermoplastic films.
Figure 7:
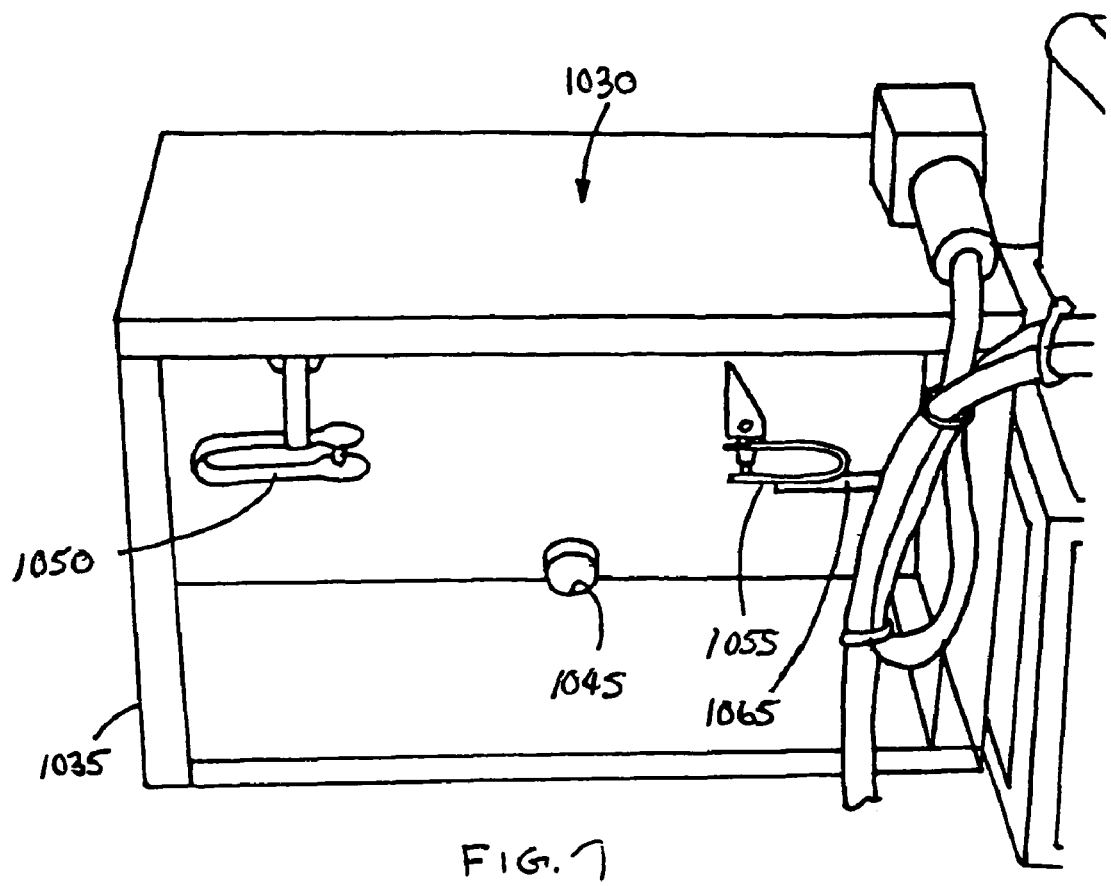
FIG. 7 is a rear perspective view showing a sound measurement chamber used in the apparatus of FIG. 6.
Figure 8:
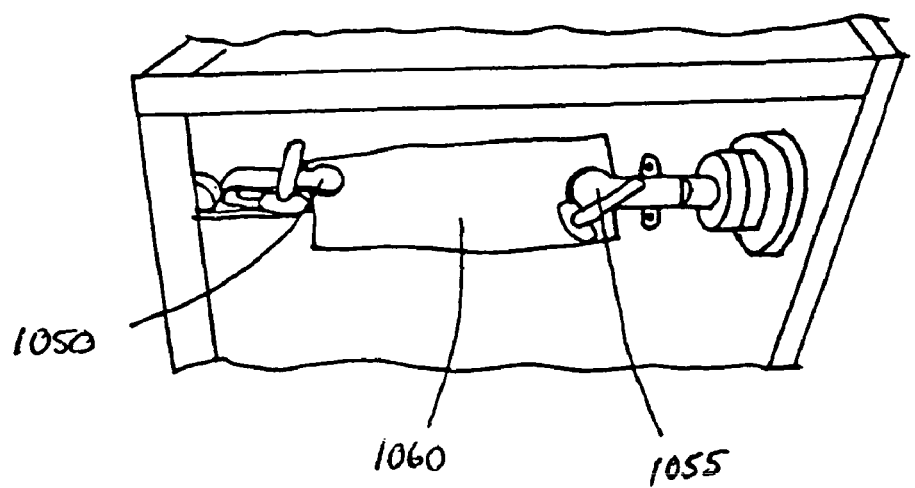
FIG. 8 is an enlarged front perspective view showing the sound measurement chamber of FIG. 7 with a non-elastic thermoplastic film sample clamped therein.

FIGS. 6-8 show a suitable sample flexing device. The testing method used is suitable for measuring noise generated by controlled flexing of a sample taken from a film. A suitable sample flexing device 1000 is shown in FIGS. 6-8. As seen most clearly in FIG. 6, the device includes a noise measurement chamber 1030, a drive mechanism 1010, and an access means 1040. The drive mechanism 1010 is designed to cyclically flex the sample through an angular displacement of 90 degrees at a frequency of 44 cycles/minute. As shown in FIGS. 6 and 7, the drive mechanism 1010 comprises an electric motor 1015 and a gear train 1020 (which includes a crank mechanism and suitable gearing so as to convert the rotary motion of motor 1015 to an oscillating motion) that are integrated to deliver the requisite angular displacement and frequency.

FIG. 7 shows the noise measurement chamber 1030 in more detail. As can be seen therein, the chamber 1030 comprises a rectangular box 1035 that is provided with access means 1040 (see FIG. 6) to allow sample insertion and removal. The box 1035 is made from LEXAN (1.27 cm thick) and has interior dimensions of 22.9 cm×15.2 cm×12.7 cm (length. width, depth). The box 1035 is also provided with sensor orifice 1045 (diameter=1.27 cm) for inserting the sensor from the audio measuring device. Inside the box 1035 is a sample holding apparatus which comprises a fixed clamp 1050 and an opposed, rotatable clamp 1055 which is connected to the gear train 1020 (see FIG. 6) by shaft 1065. The fixed clamp 1050 is attached to the end of the box 1035 that is opposite to the drive mechanism. The axes of clamps 1050 and 1055 are horizontally and vertically aligned. The leading edges of clamps 1050, 1055 are separated by a distance of approximately 10 cm. As seen more clearly in FIG. 8, the clamps 1050 and 1055 have a circular configuration (with a diameter of approximately 18 mm) for gripping the sample 1060.

The sample 1060 may be prepared using a template and an appropriate cutting device (i.e., scissors or utility knife) to cut rectangular samples from the material to be tested. For the testing described herein, rectangular samples measuring approximately 75 mm×111 mm were cut. Enough samples of each film were cut to run at least 3 tests for each.

A suitable audio measuring device is the Audio Tool Box™ marketed by TerraSonde of Bolder, Colo., may be used for measuring sound levels. The audio measurement device is set-up according to the manufacturer's instructions. Specifically, the "Acoustic Analysis, Real Time Analyzer" mode is used with the following settings:
Function: RTA (Real Time Analyzer)
Submenu: Full (20 Hz-20 KHz)
Octave-Band: 3 (⅓ Octave Band)
Averaging: 1 s (1 second)
Input: MicL (Low Range Microphone Input: 30-95 dB)
Display dB Range: 72-55
Pink Noise Generator: Off
Memory: Initial dB Settings Set-up of the sample flexing device included confirming that the drive mechanism 1010 is operating at a frequency of 44 cycles per minute and that the angular displacement during operation was approximately 90 degrees. In addition, the orientation of the clamps 1050, 1055 is checked to confirm that their open faces were angularly aligned within ±15 degrees.

For each sample, an ambient sound level is measured to allow the sample sound measurement to be compensated for noise generated by the drive mechanism 1010. The ambient sound level may be measured prior to or after evaluation of samples at each frequency of interest. To obtain an ambient sound level, the motor 1015 is started and the probe from the audio measurement device is inserted into sensor orifice 1045. The distance from the end of the probe to the centerline of the sample is measured. If necessary, adjust the distance from the end of the probe to the centerline of the sample such that the distance is approximately 63.5 mm. The audio measurement device is then set to the first frequency at which sound level is to be measured. After a 5 second stabilization period, the highest decibel reading observed over the next 5 seconds is recorded. The ambient noise measurements are identified by the variable "ASfi", where f is the frequency and i is the replicate number. The foregoing is repeated to obtain three decibel measurements. The motor 1015 is then turned off, and the audio measurement device is set to the next frequency for sound level measurement. This is repeated until sound level measurements are obtained at the desired frequencies, i.e. 2 kHz, 2.5 kHz, 3.15 kHz, 4 kHz, and 5 kHz.

To measure the noise level of each sample, first the access means 1040 and clamps 1050, 1055 are opened. A sample is placed on one of the clamps 1050, 1055 so that it is approximately centered between the clamps. The clamp is then closed. The sample is placed under a slight tension, such as approximately 10N, while the other end of the sample is placed in the remaining open clamp, and the remaining clamp is closed. The sample is then visually inspected to ensure that the long edges of the sample are parallel to the axis of clamps 1050, 1055. In addition, the sample is inspected to ensure that there was less than 15 degrees of skew between the clamps. If not, the position of rotatable clamp 1055 is manually rotated. With the sample properly oriented, the access means 1040 is closed and the motor 1015 is started. The probe of the audio measurement device is inserted into the sensor orifice 1045, and the position of the probe is adjusted as needed to obtain a distance from the end of the probe to the centerline of the sample of approximately 63.5 mm. The audio measurement device is set to the first frequency for sound level measurement. After a 5 second stabilization period, the highest decibel reading observed over the next 5 seconds is recorded. The sample sound level measurements are identified as "SjSfi", where j is a material identifier, f is the frequency and i is the replicate number. The foregoing is repeated to obtain sound level measurements for the sample at the other desired frequencies, 2 kHz, 2.5 kHz, 3.15 kHz, 4 kHz, and 5 kHz. This process is repeated for each sample, to obtain a full set of data.

The sound data is then used in well-known algorithms to obtain more meaningful information regarding the sound characteristics of the sample films. First, an average sound level for each frequency was calculated for both ambient sound and sample sound using the formula:

$$S_jS_{fAvg} = (10 \log(\Sigma 10^{(SjSfi)/10}))/n \text{ or } AS_{fAvg} = (10 \log(\Sigma 10^{(ASfi)/10}))/n$$

The average sound level for a sample, corrected for the average ambient sound, for each frequency was then calculated using the formula:

$$C_jS_f = 10(\log 10^{(SjSfAvg/10)} - 10^{(ASfAvg/10)}).$$

This concludes the test method.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A non-elastic thermoplastic film comprising:
   a noise abatement region comprising a plurality of apertures, wherein each of the plurality of apertures have an area of between about 4 mm$^2$ to about 75 mm$^2$; and
   a fastening component disposed within the noise abatement region such that the fastening component is surrounded by noise abatement elements;
   wherein the non-elastic thermoplastic film has a thickness, wherein the thickness is in a range of from about 50 μm to about 110 μm;
   wherein each of the plurality of apertures has a length of between about 3 mm to about 6 mm, and wherein each of the plurality of apertures has a width of between about 3 mm to about 6 mm;
   wherein each of the plurality of apertures are spaced apart by a first distance and a second distance, wherein the first distance is between about 3 mm to about 6 mm, and the second distance is between about 3 mm to about 6 mm.

2. The non-elastic thermoplastic film of claim 1, wherein at least one of the plurality of apertures extends through the thickness of the non-elastic thermoplastic film.

3. The non-elastic thermoplastic film of claim 2, wherein at least one of the plurality of apertures extends through only a surface of the non-elastic thermoplastic film through only a portion of the thickness of the non-elastic thermoplastic film.

4. The non-elastic thermoplastic film of claim 3, wherein the at least one of the plurality of apertures extending only through a portion of the thickness of the non-elastic thermoplastic film has a depth, and wherein the depth is in a range of about 5% to about 99% of the thickness of the non-elastic thermoplastic film.

5. The non-elastic thermoplastic film of claim 1, wherein the non-elastic thermoplastic film is selected from the group consisting of: polyurethanes, polyolefins, polystyrenes, polycarbonates, polyesters, polymethacrylates, ethylene vinyl acetate copolymers, ethylene vinyl alcohol copolymers, polyvinylchlorides, acrylate modified ethylene vinyl acetate polymers, ethylene acrylic acid copolymers, nylons fluorocarbons, and any combination thereof.

6. The non-elastic thermoplastic film of claim 1, wherein the fastening component is a slot member having a slot therein.

7. The non-elastic thermoplastic film of claim 1, wherein at least one of the plurality of apertures comprises an area of between about 20 mm$^2$ to about 50 mm$^2$.

8. The non-elastic thermoplastic film of claim 1 further comprising a first direction and a second direction, wherein a larger number of apertures are aligned in the second direction than in the first direction.

9. The non-elastic thermoplastic film of claim 8, wherein a fastening force is generally parallel to the second direction.

10. The non-elastic thermoplastic film of claim 1 further comprising a first direction and a second direction, wherein a larger number of apertures are aligned in the first direction than in the second direction.

11. A disposable absorbent article for wearing about the lower torso of a wearer, the disposable absorbent article comprising: a first waist region, a second waist region, a crotch region disposed between the first and second waist regions; a first waist edge and a second waist edge; and a first longitudinal edge and a second longitudinal edge; the disposable absorbent article further comprising:
    a topsheet;
    a backsheet attached to at least a portion of the topsheet; and
    an absorbent core disposed between the topsheet and the backsheet;
    a first pair of side panels extending outward from the first and second longitudinal edges in the first waist region, wherein each of the first pair of side panels comprises a first fastening component; and
    a second pair of side panels extending outward from the first and second longitudinal edges in the second waist region, wherein each of the second pair of side panels comprise:
       a non-elastic thermoplastic film having a noise abatement region comprising a plurality of apertures, wherein each of the plurality of apertures have an area of between about 4 mm$^2$ to about 75 mm$^2$; and
       a second fastening component disposed within the noise abatement region such that the fastening component is surrounded by noise abatement elements,
    wherein the first fastening components are capable of engaging the second fastening components thereby fastening the disposable absorbent article;
    wherein the non-elastic thermoplastic film has a thickness, wherein the thickness is in a range of from about 50 μm to about 110 μm;
    wherein each of the plurality of apertures has a length of between about 3 mm to about 6 mm, and wherein each of the plurality of apertures has a width of between about 3 mm to about 6 mm;
    wherein each of the plurality of apertures are spaced apart by a first distance and a second distance, wherein the first distance is between about 3 mm to about 6 mm, and the second distance is between about 3 mm to about 6 mm.

* * * * *